(12) United States Patent
Heinrich et al.

(10) Patent No.: US 8,480,694 B2
(45) Date of Patent: Jul. 9, 2013

(54) METHOD AND APPARATUS FOR ANASTOMOSIS INCLUDING AN EXPANDABLE ANCHOR

(75) Inventors: Russell Heinrich, Madison, CT (US); Scott E. Manzo, Shelton, CT (US)

(73) Assignee: Covidien LP, Mansfield, MA (US)

( * ) Notice: Subject to any disclaimer, the term of this patent is extended or adjusted under 35 U.S.C. 154(b) by 190 days.

(21) Appl. No.: 12/841,523

(22) Filed: Jul. 22, 2010

(65) Prior Publication Data

US 2010/0286717 A1 Nov. 11, 2010

Related U.S. Application Data

(62) Division of application No. 10/510,869, filed as application No. PCT/US03/11909 on Apr. 16, 2003, now Pat. No. 7,780,687.

(60) Provisional application No. 60/373,709, filed on Apr. 17, 2002.

(51) Int. Cl.
*A61B 17/08* (2006.01)
(52) U.S. Cl.
USPC .......................................... 606/153; 606/154
(58) Field of Classification Search
USPC .......................................... 606/151, 153–156
See application file for complete search history.

(56) References Cited

U.S. PATENT DOCUMENTS

| | | | |
|---|---|---|---|
| 2,898,913 A * | 8/1959 | Ritter et al. ................... | 604/368 |
| 4,873,977 A * | 10/1989 | Avant et al. ................ | 227/180.1 |
| 4,911,164 A | 3/1990 | Roth | |
| 4,917,089 A | 4/1990 | Sideris | |
| 4,930,502 A * | 6/1990 | Chen ............................... | 606/150 |
| 5,047,039 A * | 9/1991 | Avant et al. .................... | 606/148 |
| 5,059,211 A | 10/1991 | Stack et al. | |
| 5,122,156 A | 6/1992 | Granger et al. | |
| 5,180,392 A * | 1/1993 | Skeie et al. ................ | 623/23.64 |
| 5,222,964 A | 6/1993 | Cooper | |
| 5,403,333 A | 4/1995 | Kaster et al. | |
| 5,411,520 A | 5/1995 | Nash et al. | |
| 5,425,739 A | 6/1995 | Jessen | |
| 5,464,414 A | 11/1995 | Cziffer | |
| 5,478,353 A | 12/1995 | Yoon | |
| 5,486,187 A | 1/1996 | Schenck | |
| 5,540,701 A | 7/1996 | Sharkey et al. | |
| 5,549,619 A | 8/1996 | Peters et al. | |
| 5,549,633 A | 8/1996 | Evans et al. | |
| 5,554,162 A | 9/1996 | DeLange | |
| 5,578,044 A | 11/1996 | Gordon et al. | |

(Continued)

FOREIGN PATENT DOCUMENTS

WO  WO 03/088848  10/2003
WO  WO 2004/000093  12/2003

(Continued)

*Primary Examiner* — Darwin Erezo

(57) ABSTRACT

The present disclosure relates a device for joining a first body vessel to a second body vessel, including an inner member having a distal end portion and defining a longitudinal axis, an outer member defining a lumen dimensioned to receive the inner member therein, and a radially expandable anchor disposed at the distal end of the inner member, the expandable anchor having an initial condition wherein the expandable anchor is disposed between the outer member and the inner member and an expanded condition wherein the expandable anchor is radially larger than the expandable anchor in the initial condition.

3 Claims, 13 Drawing Sheets

U.S. PATENT DOCUMENTS

| | | | |
|---|---|---|---|
| 5,591,179 A | 1/1997 | Edelstein | |
| 5,617,878 A * | 4/1997 | Taheri | 128/898 |
| 5,634,936 A | 6/1997 | Linden et al. | |
| 5,695,504 A | 12/1997 | Gifford, III et al. | |
| 5,700,272 A | 12/1997 | Gordon et al. | |
| 5,702,412 A | 12/1997 | Popov et al. | |
| 5,702,419 A | 12/1997 | Berry et al. | |
| 5,707,380 A | 1/1998 | Hinchliffe et al. | |
| 5,741,277 A | 4/1998 | Gordon et al. | |
| 5,769,870 A | 6/1998 | Salahieh et al. | |
| 5,797,934 A | 8/1998 | Rygaard | |
| 5,817,113 A | 10/1998 | Gifford, III et al. | |
| 5,833,698 A | 11/1998 | Hinchliffe et al. | |
| 5,868,762 A | 2/1999 | Cragg et al. | |
| 5,904,697 A | 5/1999 | Gifford, III et al. | |
| 5,944,730 A * | 8/1999 | Nobles et al. | 606/151 |
| 5,951,576 A * | 9/1999 | Wakabayashi | 606/151 |
| 6,024,748 A | 2/2000 | Manzo et al. | |
| 6,048,351 A | 4/2000 | Gordon et al. | |
| 6,051,007 A | 4/2000 | Hogendijk et al. | |
| 6,063,056 A * | 5/2000 | Engelberg | 604/97.01 |
| 6,063,114 A | 5/2000 | Nash et al. | |
| 6,149,658 A | 11/2000 | Gardiner et al. | |
| 6,152,937 A | 11/2000 | Peterson et al. | |
| 6,162,244 A * | 12/2000 | Braun et al. | 623/1.12 |
| 6,171,319 B1 | 1/2001 | Nobles et al. | |
| 6,171,321 B1 | 1/2001 | Gifford, III et al. | |
| 6,176,864 B1 * | 1/2001 | Chapman | 606/153 |
| 6,203,553 B1 | 3/2001 | Robertson et al. | |
| 6,241,742 B1 | 6/2001 | Spence et al. | |
| 6,241,743 B1 * | 6/2001 | Levin et al. | 606/153 |
| 6,254,617 B1 | 7/2001 | Spence et al. | |
| 6,280,460 B1 | 8/2001 | Bolduc et al. | |
| 6,350,253 B1 * | 2/2002 | Deniega et al. | 604/164.02 |
| 6,364,856 B1 * | 4/2002 | Ding et al. | 604/103.02 |
| 6,454,780 B1 | 9/2002 | Wallace | |
| 6,517,558 B2 * | 2/2003 | Gittings et al. | 606/153 |
| 6,666,873 B1 * | 12/2003 | Cassell | 606/153 |
| 6,699,274 B2 * | 3/2004 | Stinson | 623/1.12 |
| 6,716,252 B2 * | 4/2004 | Lazarovitz et al. | 623/23.66 |
| 6,726,696 B1 | 4/2004 | Houser et al. | |
| 6,740,101 B2 * | 5/2004 | Houser et al. | 606/153 |
| 7,048,747 B2 * | 5/2006 | Arcia et al. | 606/139 |
| 7,083,631 B2 * | 8/2006 | Houser et al. | 606/153 |
| 7,105,002 B2 * | 9/2006 | Chapman | 606/153 |
| 7,182,771 B1 * | 2/2007 | Houser et al. | 606/155 |
| 7,648,515 B2 * | 1/2010 | Heinrich et al. | 606/153 |
| 7,780,687 B2 * | 8/2010 | Heinrich et al. | 606/154 |
| 2002/0032486 A1 * | 3/2002 | Lazarovitz et al. | 623/23.67 |
| 2005/0171563 A1 * | 8/2005 | Heinrich et al. | 606/153 |
| 2010/0286717 A1 * | 11/2010 | Heinrich et al. | 606/153 |

FOREIGN PATENT DOCUMENTS

| | | |
|---|---|---|
| WO | WO 2004/000134 | 12/2003 |
| WO | WO 2004/000135 | 12/2003 |
| WO | WO 2004/000136 | 12/2003 |

* cited by examiner

METHOD AND APPARATUS FOR ANASTOMOSIS INCLUDING AN EXPANDABLE ANCHOR

CROSS-REFERENCE TO RELATED APPLICATIONS

This application is a divisional of U.S. application Ser. No. 10/510,869 filed Oct. 7, 2004, now U.S. Pat. No. 7,780,687, which is a 371 of PCT/US03/11909 filed Apr. 16, 2003, which claims benefit of application No. 60/373,709 filed Apr. 17, 2002, and the disclosures of each of the above-identified applications are hereby incorporated by reference in their entirety.

BACKGROUND

1. Technical Field

The present disclosure relates to devices and methods used for joining tissue portions and, more particularly, to anastomotic devices and methods for positioning and joining tissue cavities using an expandable and/or bio-absorbable material. The present disclosure also relates to devices with anchors and methods of using the same.

2. Background of Related Art

Anastomosis is the bringing together and/or joining of two hollow or tubular structures. For example, the removal of cancerous growth or treatment of cancerous tissue can result in a need to connect two portions of organs or two body conduits in fluid communication with one another. Most body conduits are generally cylindrical in configuration and have a generally circular cross-section. When it is desired to suture such a conduit to another body conduit, typically sutures are placed around the circumference of the conduits in order to maintain their patency and in order to maintain its lumen or channel. It can be appreciated that the sutures made on top of the conduits in at least certain anastomosis procedures are made relatively easier than the sutures made underneath the conduits.

The complexity of anastomosis attachment is made manifestly apparent in a surgical procedure referred to generally as a radical prostatectomy (i.e., a well established surgical procedure for patients with localized prostatic carcinoma). Radical prostatectomy procedures, for example, require the removal of the cancerous tissue while attempting to preserve the sexual capability and continence of a patient.

The radical prostatectomy surgical procedure is generally concluded with the joining of the bladder, in particular the bladder neck, to the urethra, in particular the urethral stump, preparing and positioning the bladder and urethra for a mucosa-to-mucosa joining, and suturing the bladder neck and the urethral stump in position. This may be accomplished using minimally invasive surgery. The current radical prostatectomy procedure is hampered by poor accessibility, the friable nature of the urethra, and the close proximity of important sexual and continence related organs to the surgical site. In addition, the radical prostatectomy procedure is further complicated by the tendency of the urethral stump to retract into adjacent tissue. As a result, considerable time and effort must be expended to re-expose the urethral stump and begin the anastomosis procedure. Further complicating this procedure is the fact that the urethral stump is hidden beneath the pubic bone thus requiring that the surgeon work at a difficult angle and in positions that are uncomfortable and limiting.

Various devices have been proposed for facilitating a radical prostatectomy procedure. In U.S. Pat. No. 5,591,179 issued to Edelstein there is disclosed a suturing device including a shaft with portions defining an interior channel extending between the proximal and distal ends of the shaft. This channel includes a generally axial lumen which extends to the proximal end and a generally transverse lumen which extends from the axial lumen distally outwardly to an exit hole at the outer surface of the shaft. A needle and suture can be back loaded into the transverse lumen of the channel while a generally non-compressible member can be movably mounted in the axial lumen of the channel. At the proximal end of the shaft a handle is provided with means operative to push the member distally through the lumen to deploy or expel the needle.

In U.S. Pat. No. 4,911,164 issued to Roth there is disclosed a suture guide with a curved distal portion. This distal portion has a plurality of exterior axial grooves which can be used to align and guide a curved needle and attached suture. In order to drive the urethral stump to an accessible position, the device is provided with a plurality of outwardly extendable members which engage the lumen of the urethra. These members make it possible to push the urethral stump into approximation with the bladder neck.

In U.S. Pat. No. 5,047,039 issued to Avant et al. there is disclosed a surgical device for the ligation of a dorsal vein and subsequent anastomosis. This device contains a pair of enclosed needles each having an attached suture which needles may be driven from the shaft of the device into adjacent tissue.

In addition, surgical anastomosis instruments having a "one shot" approach for quickly securing two vessel portions have been developed and include end-to-side anastomosis instruments which are typically used in the aortic and coronary regions of the body. End-to-end and side-to-side anastomosis instruments for joining vessel portions together are also well known. These instruments typically use metal fasteners or staples having a "U" or a "C" shape to join the tissue portions to one another. There are applications, however, such as with the urethra, where the use of metal fasteners or staples are known to increase the likelihood of future complications.

Accordingly, a continuing need exists for anastomosis devices for performing procedures such as a radical prostatectomy that can position one vessel portion, e.g., the bladder and/or bladder neck, adjacent a second vessel portion, e.g., the urethra and/or urethral stump, for anastomosis minimizing or avoiding the use of sutures, clips and/or staples.

SUMMARY

The present disclosure relates to anastomotic devices and methods for performing surgical anastomosis of tissue cavities.

According to one aspect of the present disclosure, a device for joining a first body vessel and a second body vessel includes an inner member having a distal end and defining a longitudinal axis, an outer member defining a lumen dimensioned to receive the inner member therein, and a radially expandable anchor disposed at the distal end of the inner member, the expandable anchor having an initial condition wherein the anchor is disposed between the outer member and the inner member and an expanded condition wherein the anchor is radially larger than the anchor in the initial condition.

Preferably, the expandable anchor is made from at least one of a sponge-like and foam-like material. More preferably, the expandable anchor is made from a bio-absorbable material. It is envisioned that the expandable anchor has a frusto-conical shape when in the expanded condition, wherein a distal end portion of the expandable anchor is radially larger than a proximal end portion of the expandable anchor. It is contemplated that the expandable anchor radially expands upon contact with moisture.

It is envisioned that the inner member comprises an inner tubular sleeve defining a central lumen extending therethrough. Preferably, the inner tubular sleeve includes a region near its distal end which is porous to permit moisture which is transmitted, via the central lumen, to the expandable anchor.

Preferably, the expandable anchor is arranged, when in the expanded condition, to permit liquid to pass therethrough and drain through the inner tubular sleeve. It is envisioned that the expandable anchor defines at least one longitudinally oriented passage extending completely therethrough when in the expanded condition.

It is contemplated that the anastomotic device further includes a control unit, remotely located, for operating the device.

It is further contemplated that the anastomotic device includes a sheath disposed about the expandable anchor for defining the shape of the expandable anchor when in the expanded condition.

Anastomotic device further includes a grasper operatively connected to the distal end of the inner tubular sleeve.

It is envisioned that the expandable anchor is fabricated from a bio-absorbable material, wherein the material dissolves after a predetermined period of time.

According to another aspect of the present disclosure, a device for performing a surgical anastomosis includes a pair of concentric tubular sleeves including an outer sleeve and an inner sleeve, each of the pair of concentric tubular sleeves having a distal end portion and a proximal end portion, and a radially expandable anchor operatively disposable between the distal end portions of the pair of concentric tubular sleeves.

Preferably, the expandable anchor is fabricated from at least one of a foam-like and sponge-like material. It is envisioned that the expandable anchor has an initial condition for insertion of the anastomotic device through a body lumen and an expanded condition which inhibits withdrawal of the anastomotic device from the body lumen. The expandable anchor is expanded from the initial condition to the expanded condition by application of a fluid thereto. Preferably, the expandable anchor has a frusto-conical shape when in the expanded condition and a thin-walled cylindrical shape when in the initial condition. It is envisioned that the expandable anchor defines at least one longitudinally oriented passage extending entirely therethrough when in the expanded condition.

Preferably, the inner tubular sleeve of the pair of concentric sleeves includes a region of porosity formed near the distal end thereof. According to one aspect of the disclosure, the region of porosity to transmit a fluid to the expandable anchor. Preferably, the inner tubular sleeve includes at least one longitudinally oriented lumen extending therethrough, wherein the lumen is configured and adapted to transmit the fluid to the plurality of perforations.

According to a further aspect of the present disclosure, a method of performing a surgical anastomosis is disclosed. The method includes the steps of providing a device for performing the surgical anastomosis including a member having a distal end portion, a radially expandable anchor operatively disposed at the distal end portion of the member, and a cover disposed over the radially expandable anchor.

The method further including the steps of passing the device through an opening in a first body vessel and into a second body vessel such that a distal end portion of the expandable anchor is positioned at least partially within the second body vessel, withdrawing the cover to expose at least the distal end portion of expandable anchor, expanding at least the distal end portion of the expandable anchor within the second body vessel such that the expandable anchor engages the second body vessel, moving the device until the second body vessel contacts a distal end of the first body vessel and a proximal end portion of the expandable anchor is positioned at least partially within the distal end of the first body vessel, withdrawing the cover to expose the proximal end portion of the expandable anchor, and expanding the proximal end portion of the expandable anchor within the distal end of the first body vessel such that the expandable anchor engages the distal end of the first body vessel.

It is envisioned that the expanding includes the introduction of a fluid to the expandable anchor.

Preferably, the expandable anchor is fabricated from at least one of a foam-like and sponge-like material. The expandable anchor is expanded by application of liquid thereto. Preferably, the expandable anchor has a frusto-conical shape when in an expanded condition. It is envisioned that the expandable anchor has a thin-walled cylindrical shape when in a compressed condition.

It is further envisioned that the member comprises an inner tubular sleeve having a region of porosity formed near the distal end thereof and the liquid is introduced through the sleeve, through the region of porosity, to the expandable anchor. Preferably, the step of moving comprises approximating a body organ and a body lumen.

According to another aspect of the present disclosure, an anchoring device is disclosed including a member having a distal end, a radially expandable anchor disposed at the distal end of the member, and a cover disposed over the radially expandable anchor to maintain the radially expandable member in an initial pre-expanded condition.

It is envisioned that the cover includes a tubular sleeve having a lumen sized to receive the member and the radially expandable anchor. The radially expandable anchor is sized so that upon removal of the cover, the anchor expands. The radially expandable anchor includes a sponge that radially expands upon the introduction of a fluid.

According to another aspect of the present disclosure, a method of deploying an anchoring device is disclosed including providing an expandable anchor, the expandable anchor being expandable upon introduction of a fluid, introducing the fluid to a first portion of the expandable anchor so that the first portion is expanded and a second portion of the expandable anchor remains in the pre-expanded configuration, and introducing the fluid to the second portion of the expandable anchor so that the second portion is expanded.

It is envisioned that the expandable anchor includes a sponge and the fluid comprises a liquid. It is further envisioned that the expandable anchor comprises a membrane expanded upon introduction of the fluid. The first portion engages a body vessel upon expansion.

The method further includes the step of moving the expandable anchor, after the first portion is expanded, so that a second body vessel is adjacent the second portion. The second portion engages the second body vessel upon expansion.

These objects together with other objects of the disclosure, along with various features of novelty which characterize the disclosure, are pointed out with particularity in the claims annexed to and forming a part of this disclosure.

BRIEF DESCRIPTION OF THE DRAWINGS

By way of example only, preferred embodiments of the present disclosure will be described herein with reference to the accompanying drawings, in which.

DETAILED DESCRIPTION OF PREFERRED EMBODIMENTS

Figure 1:
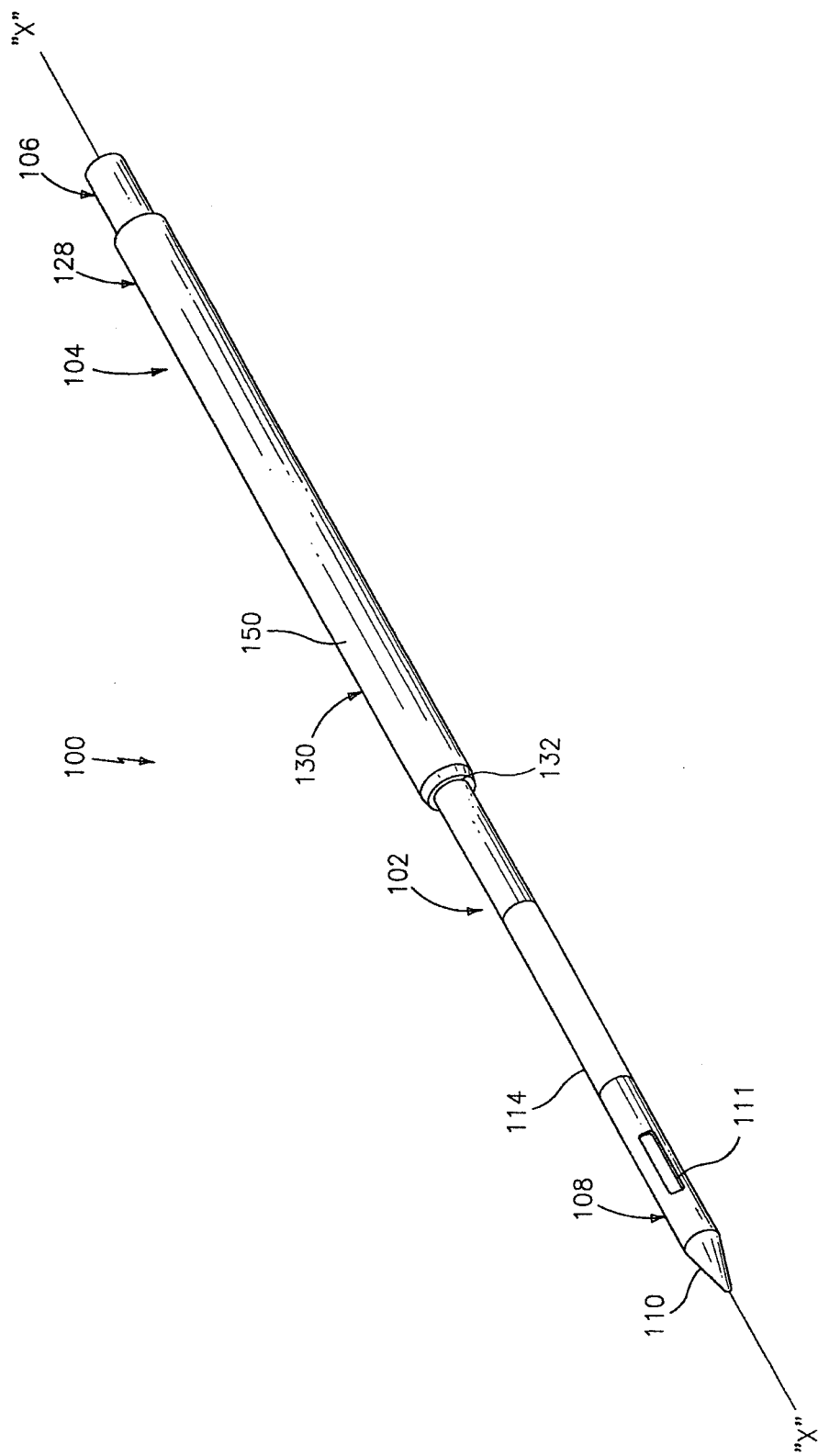
FIG. 1 is a perspective view of a device for performing an anastomotic procedure, in accordance with an embodiment of the present disclosure, shown in an insertion and/or a withdrawal condition.
Figure 2:
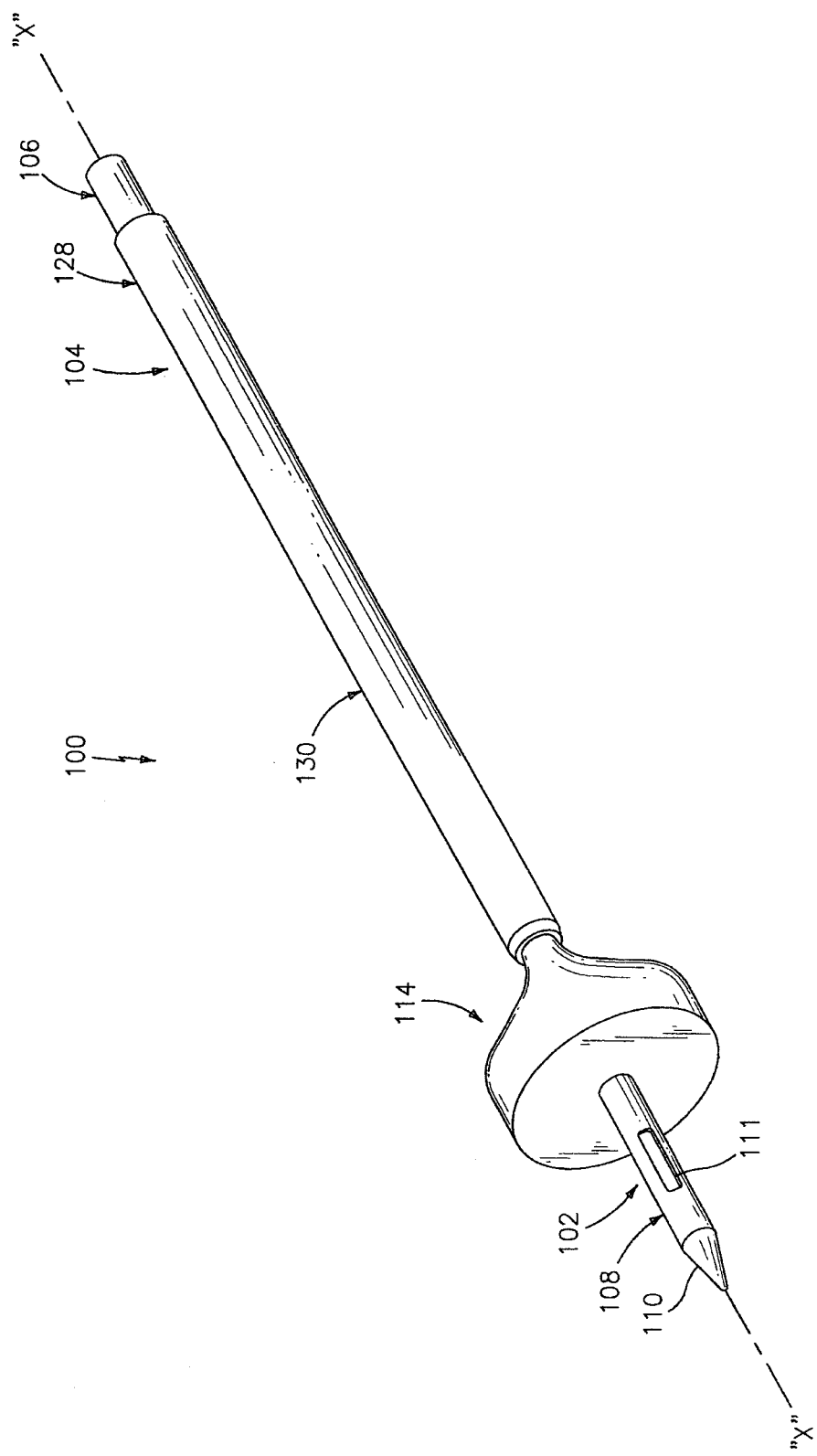
FIG. 2 is a perspective view of an anastomotic device according to the embodiment of FIG. 1, shown in a partially deployed condition.

Preferred embodiments of the presently disclosed anastomotic device will now be described in detail with reference to the drawing figures wherein like reference numerals identify similar or identical elements. In the drawings and in the description which follows, the term "proximal", as is traditional will refer to the end of the surgical applier which is closest to the operator, while the term "distal" will refer to the end of the applier which is furthest from the operator.

Referring to FIGS. 1-11, in which like reference numerals identify similar or identical elements throughout the several views, embodiments of devices for performing anastomotic procedures, in accordance with the principles of the present disclosure, are shown generally as reference numeral 100. Although device 100 offers significant advantages to a radical prostatectomy procedure, it will be understood that the device is applicable for use in any anastomotic procedure where two hollow or tubular structures are joined, such as when the end of a conduit is to be sutured or otherwise secured to a hollow body organ.

Referring now in specific detail to the drawings in which like reference numerals identify similar or identical elements throughout the several views, and initially to FIG. 1, anastomotic device 100 is shown in a first condition (i.e., insertion and/or withdrawal condition) configured for passage through a body lumen and into a body cavity. Anastomotic device 100 includes a pair of concentric tubular sleeves, preferably, an inner tubular sleeve 102 and an outer tubular sleeve 104 slidably disposed about inner tubular sleeve 102, and a radially expandable anchor 114 configured and adapted to be disposed about inner tubular sleeve 102.

Inner tubular sleeve 102 includes a proximal end 106 and a distal end 108. Preferably, distal end 108 is provided with a conical cap 110 in order to facilitate insertion of device 100 through the body lumen. Outer tubular sleeve 104 includes a proximal end 128 and a distal end 130 defining a lumen 132 extending therethrough, in which inner tubular sleeve 102 is slidably disposed.

It is contemplated that inner tubular sleeve 102 includes at least one opening 111 formed near distal end 108 which opening 111 provides access to a central lumen 112 (see FIGS. 5, 7, 9 and 11). Central lumen 112 of inner tubular sleeve 102 defines a central longitudinal axis "X". If needed, opening 111 and central lumen 112 function much like a Foley-type catheter and permit fluid to be drained from or infused into the target operative site and/or define an access channel through which optical instruments can be passed through in order to aid in the viewing of surrounding tissue.

Radially expandable anchor 114 is preferably a sponge-type and/or foam-type anchor having an initial condition (i.e., low profile, compressed, etc.) when dry and a subsequent expanded condition (i.e., enlarged profile) when wet. The material of anchor 114 is selected such that anchor 114 has the required flexibility, structural integrity and composition suitable for internal anastomotic applications. Anchor 114 may be fabricated from a bioabsorbable material, which can be completely absorbed into the body of the patient after a sufficient amount of time has lapsed, to permit a sufficient amount of healing to have taken place between the body cavity and the body lumen.

Figure 3:
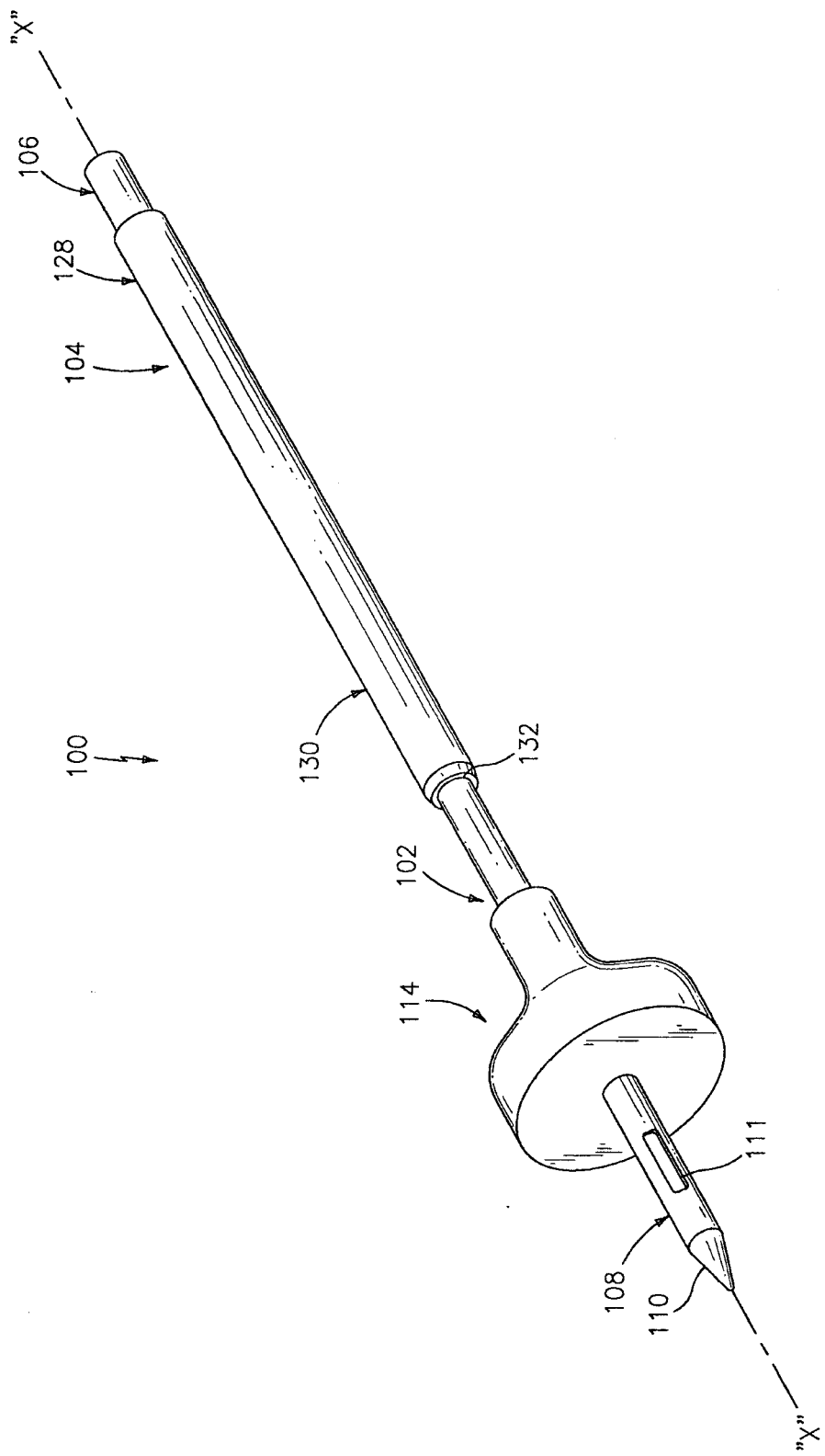
FIG. 3 is a perspective view of an anastomotic device according to the embodiment of FIGS. 1 and 2, shown in a fully deployed or anchoring condition.

Preferably, as seen in FIG. 1, when in the initial condition, anchor 114 has a substantially hollow thin-walled cylinder like configuration and when in the fully expanded condition, as seen in FIG. 3, anchor 114 is larger and desirably has a substantially frusto-conical and/or bell-shaped outer profile. In use, anchor 114 expands from the initial condition to the expanded condition upon addition of moisture, fluid or liquid (e.g., water, saline, sterile water and the like) thereto. The fluid may comprise any bio-compatible fluid for expanding anchor 114.

The fluid can be applied to anchor 114 from an external discrete source of fluid (not shown), such as, for example, a syringe. Preferably, inner tubular sleeve 102 and/or outer tubular sleeve 104 include fluid transmission regions which are configured and adapted to distribute the liquid to specific locations along the length and around the circumference of anchor 114 in order to control the rate of expansion of anchor 114 and the initial location of expansion of anchor 114.

For example, the fluid transmission region may be a region of porosity provided at near distal end 108 of inner tubular sleeve 102, having a length substantially equal to the length of anchor 114, which extends at least partially around and, preferably, entirely around the circumference of inner tubular sleeve 102. In this manner, fluid can be introduced to the porous region, via central lumen 112, which is in turn transmitted to and absorbed by an inner surface of anchor 114 in order to cause anchor 114 to expand radially thereabout along the entire length thereof.

Alternatively, the fluid transmission region may include a plurality of annular regions of porosity, extending the length of anchor 114, provided near distal end 108 of inner tubular sleeve 102 and defining a plurality of discrete annular fluid transmission zones each of which are independently connected to a source of fluid. In this manner, anchor 114 can be expanded as desired by transmitting a fluid to a desired and/or selected one or more than one fluid transmission zone, or more than one fluid transmission zone, to the inner surface of anchor 114 in order expand anchor 114 as desired.

It is further envisioned, as seen in FIGS. 5, 7, 9 and 11, that the fluid transmission region can include a plurality of perforations 120 formed near distal end 108 and extending through to central lumen 112 of inner tubular sleeve 102. In this manner, anchor 114 can be expanded by transmitting a fluid, through central lumen 112 and through perforations 120 to the inner surface of anchor 114.

The above examples are intended to be merely illustrative of specific configurations of fluid transmission regions which are capable of transmitting fluid to the inner surface of anchor 114 and are in no way intended to be limiting. It is understood that other configurations of transmitting fluid to the inner surface of anchor 114 can be used without departing from the scope and breath of the present disclosure.

Figure 4:
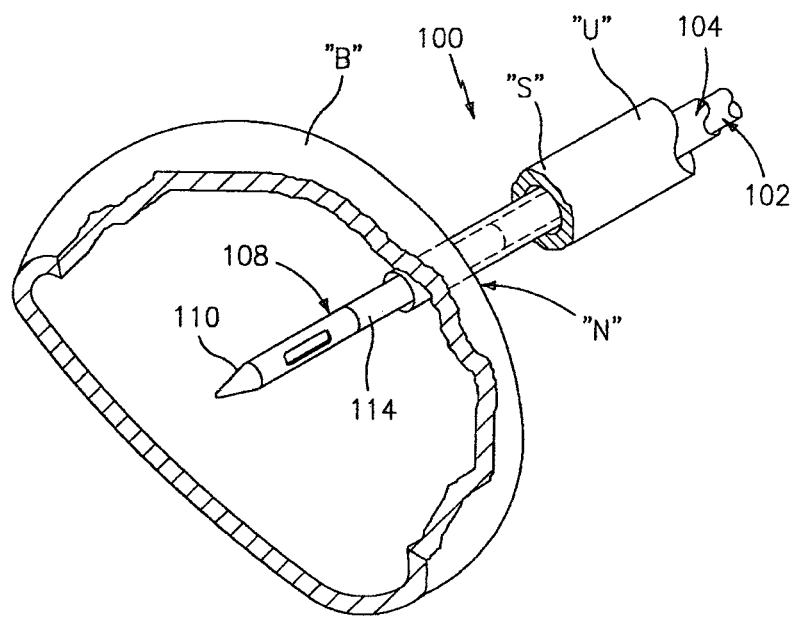
FIG. 4 is an enlarged perspective view of a distal end of an anastomotic device in accordance with the embodiment of FIGS. 1-3, shown in the insertion or withdrawal condition, within a portion of a urinary system.
Figure 5:
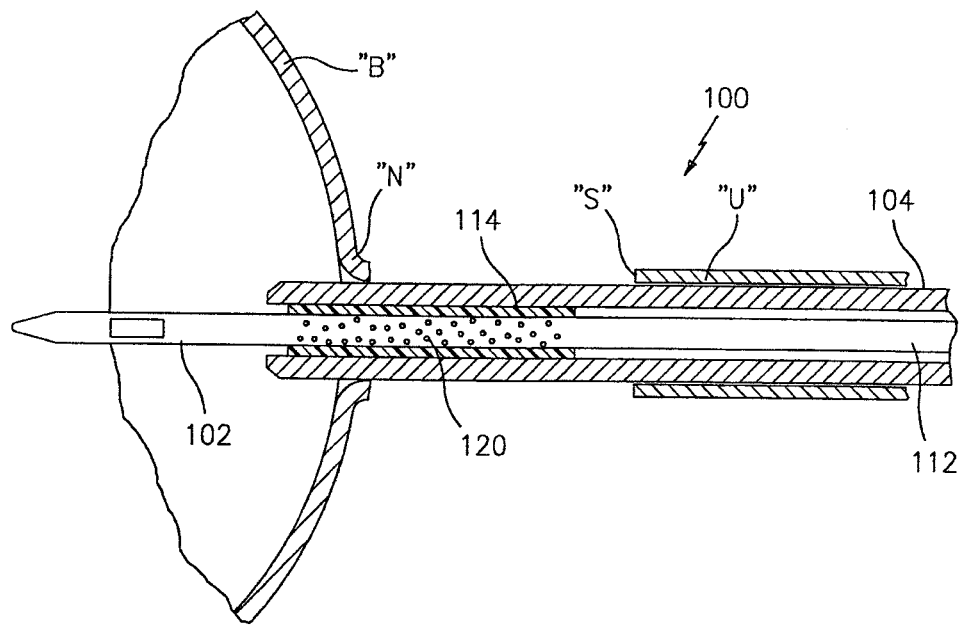
FIG. 5 is a partial cross-sectional side elevational view of a urinary system illustrating the insertion of an anastomotic device in accordance with the embodiment of FIGS. 1-4, in the insertion condition, through the urethra and into the bladder.

As seen in FIG. 1 and, in particular, FIGS. 4 and 5, anchor 114 is positioned on inner tubular sleeve 102 near distal end 108 while in the initial condition. In the embodiment shown, anchor 114 is positioned over a fluid transmission region (i.e., perforations 120) of inner tubular sleeve 102. Outer tubular sleeve 104 is then positioned along inner tubular sleeve 102 such that distal end 130 of outer tubular sleeve 104 is preferably positioned beyond the distal most end of anchor 114 (see FIG. 5). In this manner, outer tubular sleeve 104 prevents fluid or moisture from prematurely coming into contact with the outer surface of anchor 114 as anastomosis device 100 is inserted through the body lumen and into the body cavity, thereby causing anchor 114 to prematurely expand.

As will be discussed in greater detail below, in use, fluid can be introduced to the inner surface of anchor 114 either before, during or after removal of outer tubular sleeve 104 from around anchor 114. It is envisioned that outer tubular sleeve 104 prevents radial expansion of anchor 114 in the event that anchor 114 prematurely begins to absorb moisture or fluid.

Turning now to FIGS. 4-11, a preferred method of use and operation of anastomotic device 100, in a radical prostatectomy procedure, will now be described in greater detail. With the prostate removed, it is preferable that the bladder neck "N" of bladder "B" is first reconstructed by everting the inner mucosal lining of bladder "B" and suturing the inner mucosal lining down to the outer wall of bladder "B" using known surgical techniques. Likewise, urethral stump "S" of urethra "U" is reconstructed by everting the inner mucosal lining of urethral stump "S" and suturing the inner mucosal lining down to the outer wall of urethra "U", using known surgical techniques.

Preferably, with bladder neck "N" reconstructed, bladder neck "N" is sized to properly accommodate and retain distal end 108 of inner sleeve 102 within bladder "B" using a standard tennis racket type closure (i.e., the opening of the bladder neck constituting the head of the tennis racket and a radial incision extending from the bladder neck constituting the handle portion of the tennis racket). For example, blabber neck "N" may be sized to match the urethra diameter.

As seen in FIGS. 4 and 5, with bladder neck "N" reconstructed, anastomotic device 100 is passed trans-urethrally through urethra "U" until distal end 108 of inner tubular sleeve 102 extends out of urethral stump "S" and into bladder "B" through bladder neck "N" as indicated by arrow "A". Preferably, anastomotic device 100 is configured such that anchor 114 is positioned around inner tubular sleeve 102 while in the initial condition and outer tubular sleeve 104 is positioned about anchor 114. In particular, distal end 108 of inner tubular sleeve 102 is preferably positioned such that distal end 130 of outer tubular sleeve 104 and, more particularly, a distal portion of anchor 114, are disposed within bladder "B" while a proximal end of anchor 114 extends out of bladder "B".

Figure 6:
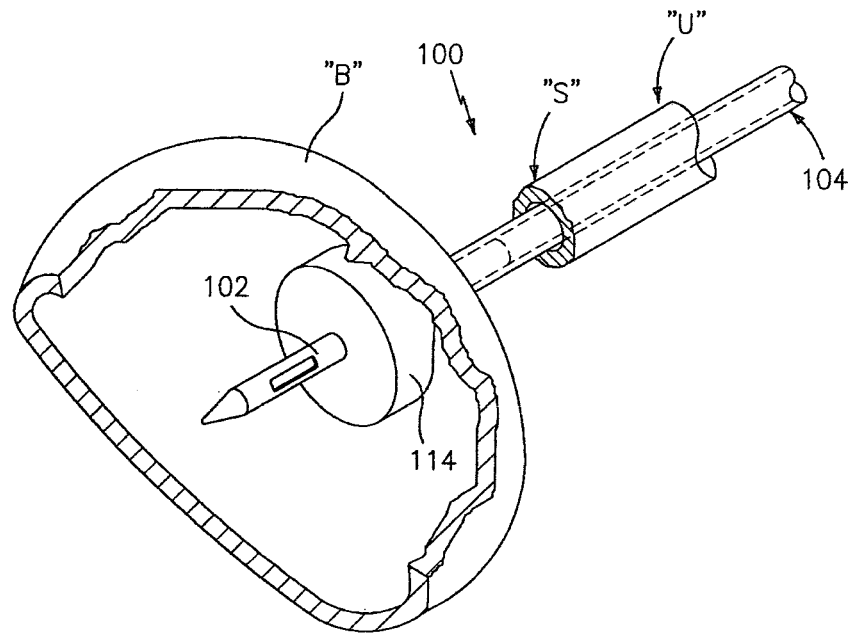
FIG. 6 is an enlarged perspective view of the distal end of an anastomotic device in accordance with the embodiment of FIGS. 1-5, shown in a bladder anchoring condition, within a portion of a urinary system.
Figure 7:
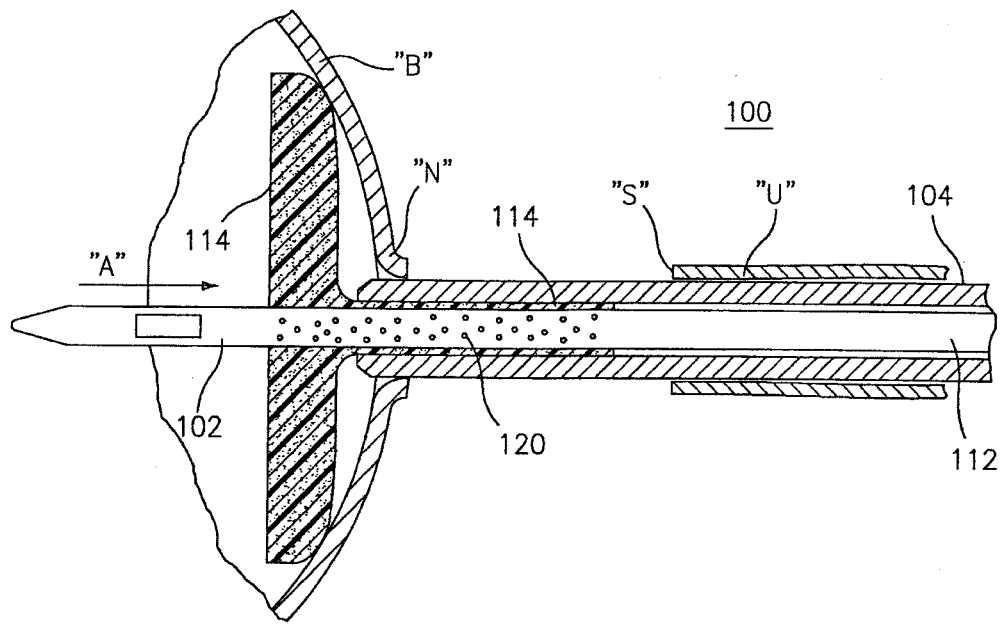
FIG. 7 is a partial cross-sectional side elevational view of the urinary system illustrating an anastomotic device in accordance with the embodiment of FIGS. 1-6, in the bladder anchoring condition, within the bladder.

Turning now to FIGS. 6 and 7, with anastomotic device 100 so positioned, outer tubular sleeve 104 is withdrawn in a proximal direction. Desirably, the distal end portion 114a of anchor 114 is exposed and a proximal end portion 114b is covered by the outer sleeve 104. With the distal end portion 114a of anchor 114 exposed, a fluid is transmitted to anchor 114 and, more preferably, to the distal end portion of anchor 114. The addition of the fluid will cause the distal end portion of anchor 114 to expand radially outward to its expanded condition which is many times greater than when in its initial condition. Preferably, fluid is transmitted to the inner surface of the distal end portion of anchor 114 as discussed above, however, it is envisioned that fluid can be transmitted to the outer surface of the distal end portion of anchor 114 by transmitting the fluid through the central lumen 112, out through opening 111 formed in distal end 108 of inner tubular sleeve 102. It is further envisioned that fluid can be transmitted to the outer surface portion of anchor 114 via a number of other know methods, such as, for example, use of a syringe. Radially expansion of the distal end of anchor 114 results in the inner surface of anchor 114 squeezing and/or constricting around inner tubular sleeve 102 and the outer surface of anchor 114 expanding to an outer circumferential diameter which is greater than the opening in bladder "B" resulting in a radial compressive force being exerted on at least a portion of anchor 114 by bladder "B". Accordingly, when in the expanded condition, anchor 114 will inhibit withdrawal or prevent withdrawal of inner tubular sleeve 102 from bladder "B".

Figure 8:
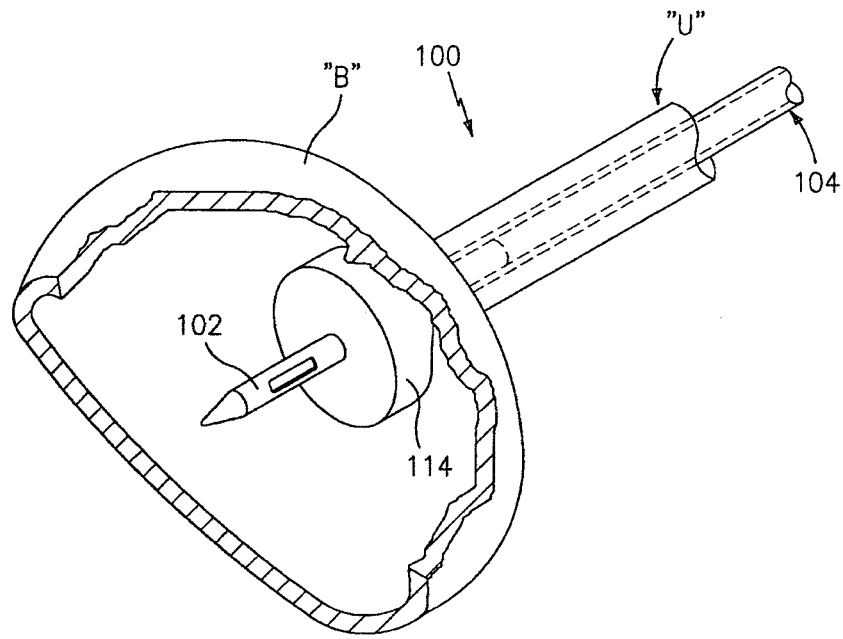
FIG. 8 is an enlarged perspective view of an anastomotic device in accordance with the embodiment of FIGS. 1-7, shown in a bladder anchoring condition with the bladder and urethra in approximation with one another.
Figure 9:
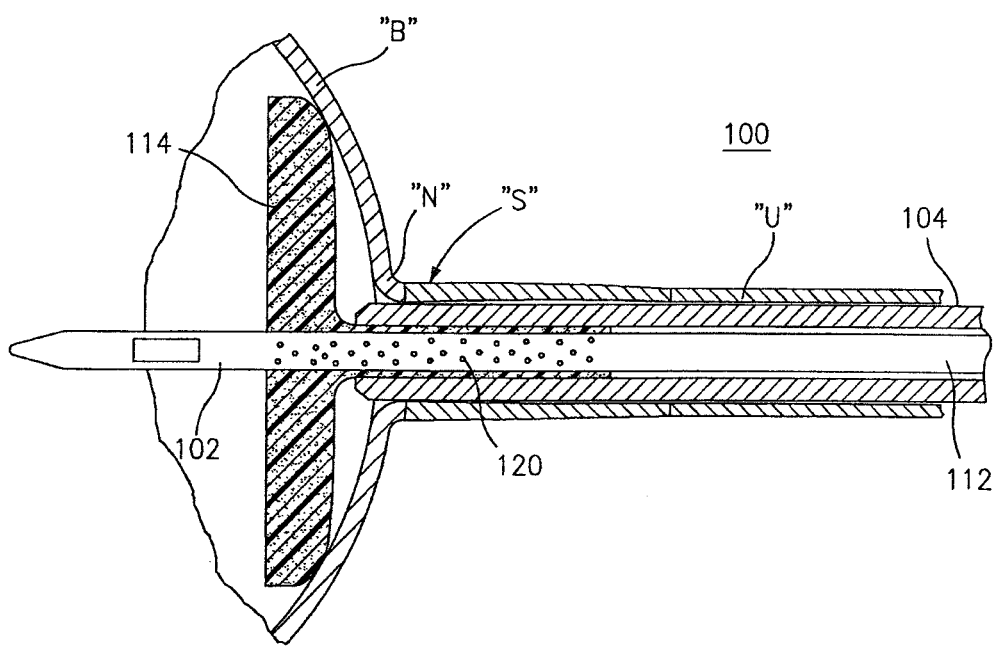
FIG. 9 is a partial cross-sectional side elevational view of a urinary system illustrating an anastomotic device in accordance with the embodiment of FIGS. 1-8, in the bladder anchoring condition, with the bladder and urethra in the approximated condition.

With anchor 114 in an expanded condition, as seen in FIGS. 8 and 9, both inner tubular sleeve 102 and outer tubular sleeve 104 are withdrawn in a proximal direction, as indicated by arrow "A" of FIG. 7. As inner and outer tubular sleeves 102 and 104 are withdrawn in direction "A", bladder "B" is also moved in direction "A" and approximated toward urethra "U".

Figure 10:
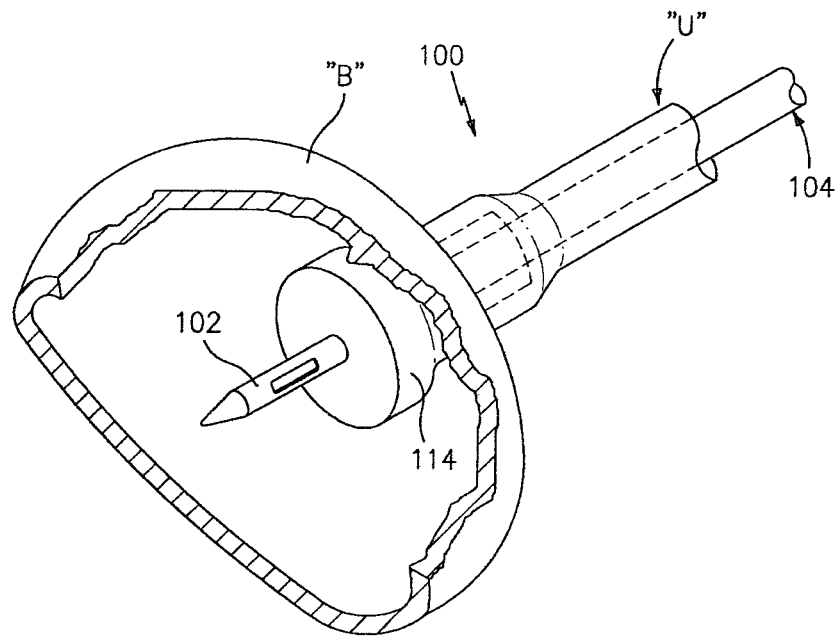
FIG. 10 is an enlarged perspective view of the distal end of an anastomotic device in accordance with the embodiment of FIGS. 1-9, while in the fully deployed condition, with the bladder and urethra in approximation with one another.
Figure 11:
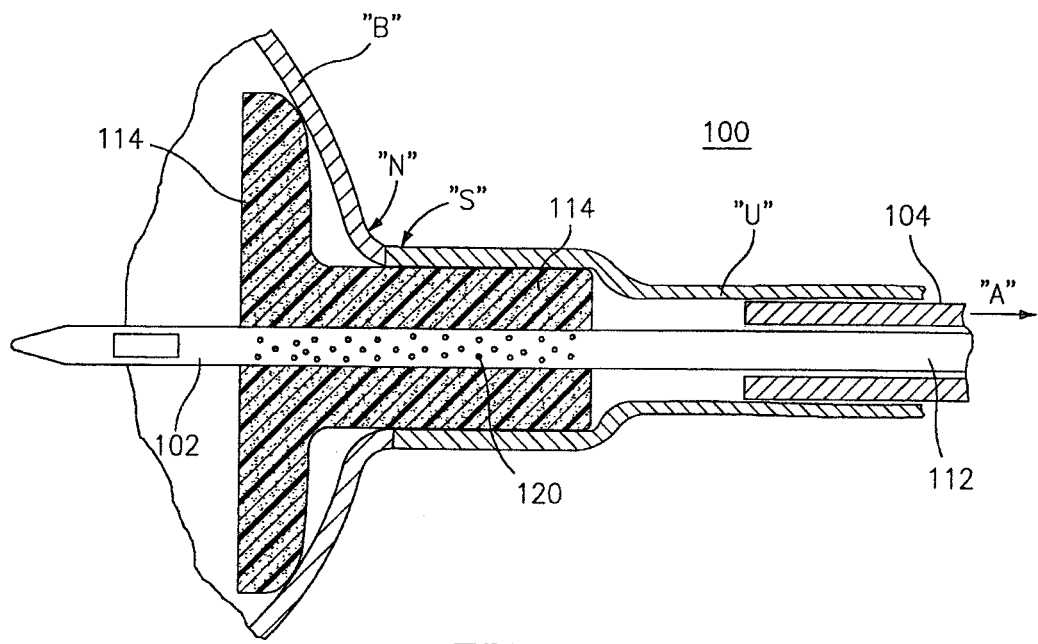
FIG. 11 is a partial cross-sectional side elevational view of a urinary system illustrating an anastomotic device in accordance with the embodiment of FIGS. 1-10, in the fully deployed condition, with the bladder and urethra in approximation with one another.

As seen in FIGS. 10 and 11, with bladder "B" and urethra "U" approximated toward one another, outer tubular sleeve 104 is further withdrawn in a proximal direction, as indicated by arrow "A" of FIG. 11. Preferably, outer tubular sleeve 104 is withdrawn a distance sufficient to entirely expose the proximal end portion 114b of anchor 114 which remains in a compressed condition (i.e., the proximal end portion). With the proximal end portion of anchor 114 exposed, fluid is transmitted, preferably to the inner surface of the proximal end portion of anchor 114 to thereby radially expand the proximal end portion of anchor 114. Once again, anchor 114 expands radially inward thereby constricting against the outer surface of inner tubular sleeve 102 and expands radially outward thereby radially pressing against the inner surface of urethra "U" resulting in a radial compressive force being exerted on at least a portion of anchor 114 by bladder "B".

Thus, with anchor 114 in a fully expanded condition, bladder "B" and urethra "U" are maintained approximated to one another. Inner tubular sleeve 102 can be left in place and function much like a catheter (i.e., a Foley-type catheter) for draining fluid from bladder "B". Alternatively, inner tubular sleeve 102 can be withdrawn from anchor 114 and ultimately from bladder "B" and urethra "U". The outer surface of inner tubular sleeve 102 may be provided with mechanical advantage structures (not shown) to facilitate withdrawal of inner tubular sleeve 102 from anchor 114, such as, for example, helical threads, which enable inner tubular sleeve 102 to exert an axial force on anchor 114 and which enables inner tubular sleeve 102 to be withdrawn from anchor 114 by simply rotating inner tubular sleeve 102 about longitudinal axis "X".

If inner tubular sleeve 102 is withdrawn from anchor 114, it is envisioned that anchor 114 is made from a material having sufficient porosity to permit fluid to travel therethrough and permit bladder "B" to drain. Alternatively, as will be described in greater detail below, when anchor 114 is in the expanded condition anchor 114 will define a plurality of lumens or passageways (see FIG. 13) extending longitudinally entirely therethrough. It is further envisioned that, if inner tubular sleeve 102 is to be withdrawn from anchor 114, that anchor 114 can be provided with a central tubular rigid/ semi-rigid liner (not shown) through which inner tubular sleeve 102 is permitted to pass. The inner surface of liner and/or the outer surface of inner tubular sleeve 102 can be provided with mechanical advantage structure to permit inner tubular sleeve 102 to withdraw anchor 114 in a proximal direction and to permit facilitated disengagement of inner tubular sleeve 102 from anchor 114. It is further envisioned that liner can include a plurality of perforations to permit transmission of fluid to the interior of anchor 114.

As described above, in certain embodiments, in certain embodiments, the anchor 114 is fabricated from a bio-absorbable material (e.g., polyglycolic acid and/or polylactic acid) and preferably, a bio-absorbable expandable/compressible foam material. In this manner, anchor 114 will be absorbed into the body after sufficient time has lapsed to permit the anastomosis between bladder "B" and urethra "U" to take place and to thereby eliminate the need for the patient to return to the doctor for a follow up procedure to remove anchor 114.

After the body vessels (such as bladder and urethra in FIG. 5) are approximated, the body vessels may be secured utilizing any appropriate fixation devices, such as staples, sutures, adhesives or any devices. However, the anchor may be relied upon to secure the body vessels while the body vessels heal.

Turning now to FIGS. 12-17, an alternative embodiment of an anastomotic device in accordance with the present disclosure is shown generally as 200. Anastomotic device 200 includes an inner tubular sleeve 202, an outer tubular sleeve 204, a radially expandable sponge 214, and a control portion 290.

Figure 13:
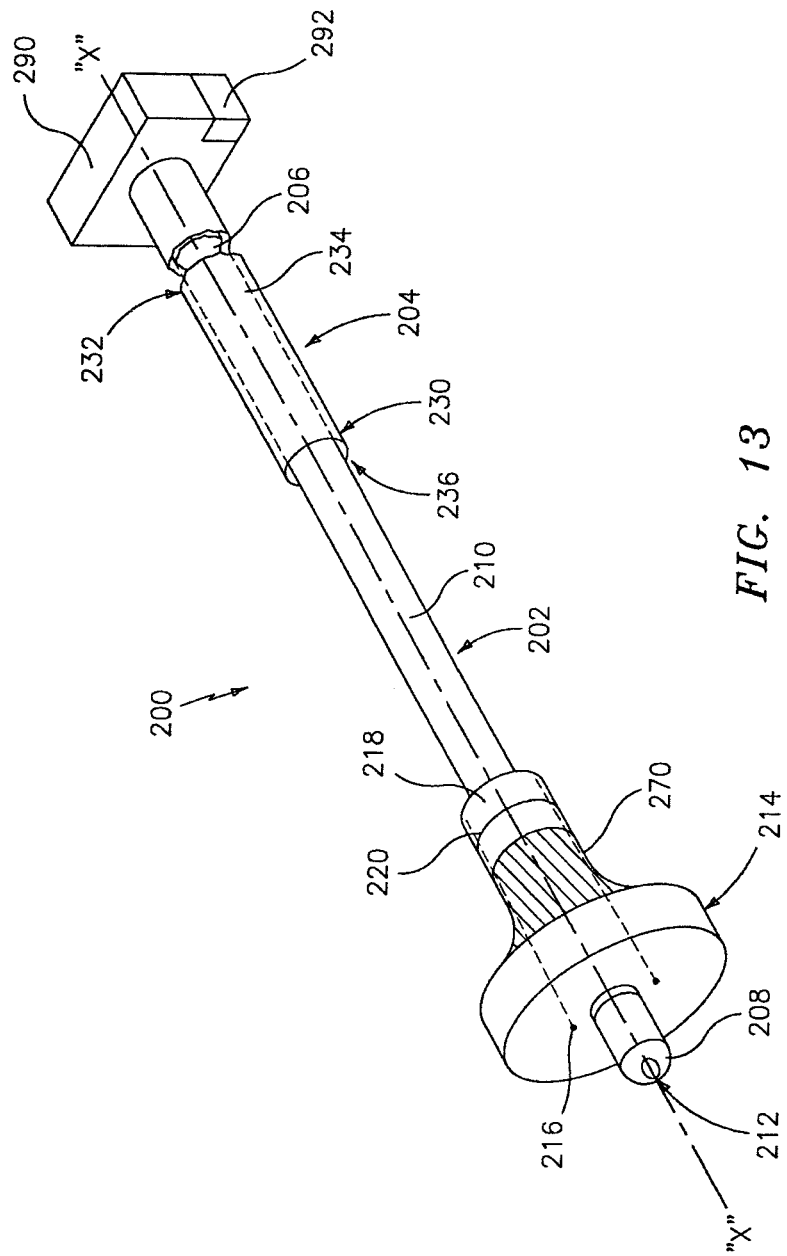
FIG. 13 is a perspective view of an anastomotic device in accordance with the embodiment of FIG. 12, shown in a fully deployed or anchoring condition.

Referring now to FIG. 13, outer tubular sleeve 204 includes a distal end portion 230, a proximal end portion 232, and a tubular body portion 234 including a central lumen 236 defining a central longitudinal axis "X". Proximal end portion 232 of outer tubular sleeve 204 is operatively connected to control portion 290.

Inner tubular sleeve 202 includes a distal end portion 208, a proximal end portion 206, and a tubular body portion 210 defining a lumen 212 therethrough. Preferably, lumen 212 is co-axially aligned with longitudinal axis "X". Inner tubular sleeve 202 is a standard catheter used in vessel applications, such as, for example, a Foley-type catheter, including certain modifications for the controlled dissemination of a fluid. Inner tubular sleeve 202 is configured and adapted to be operatively connected to and, preferably, in fluid communication with control portion 290.

As seen in FIG. 13, control portion 290 is in fluid communication with a source of fluid and/or aspiration 292 for the administration and/or withdrawal of fluids to/from inner tubular sleeve 202.

It is envisioned that tubular body portion 210 of inner tubular sleeve 202 includes regions suitable for the positioning of expandable anchor 214. Similar to anastomotic device 100 described above, tubular body portion 210 can be porous or include a plurality of perforations in communication with a plurality of channels suitable for disbursing fluid to anchor 214 or to selected portions of anchor 214 using separate and independent channels.

Anchor 214 comprises an expandable structure and may comprise a sponge. Anchor 214 is preferably fabricated from a foam type material having an initial condition when first mounted onto tubular body portion 210 and, after contact with a sufficient amount of fluid or moisture, an expanded condition wherein anchor 214 is expanded to a larger structure. Preferably, the foam type material selected for anchor 214 has the required flexibility and structural integrity suitable for internal anastomotic medical applications. In one preferred embodiment, anchor 214 is composed of a bio-absorbable foam type material. It is envisioned that the material of anchor 214 can be selected such that when in the expanded condition, anchor 214 has sufficient porosity so that fluid is drained through anchor 214 and through inner tubular sleeve 202 and precludes the necessity of inner tubular sleeve 202 being configured as a catheter.

As best seen in FIG. 13, anchor 214, in certain preferred embodiments, is arranged to form a plurality of longitudinally oriented passageways or channels 216 generally aligned with the longitudinal axis "X" and suitable for the passage of liquids, such as, for example, discharge from the bladder, therethrough.

Figure 12:
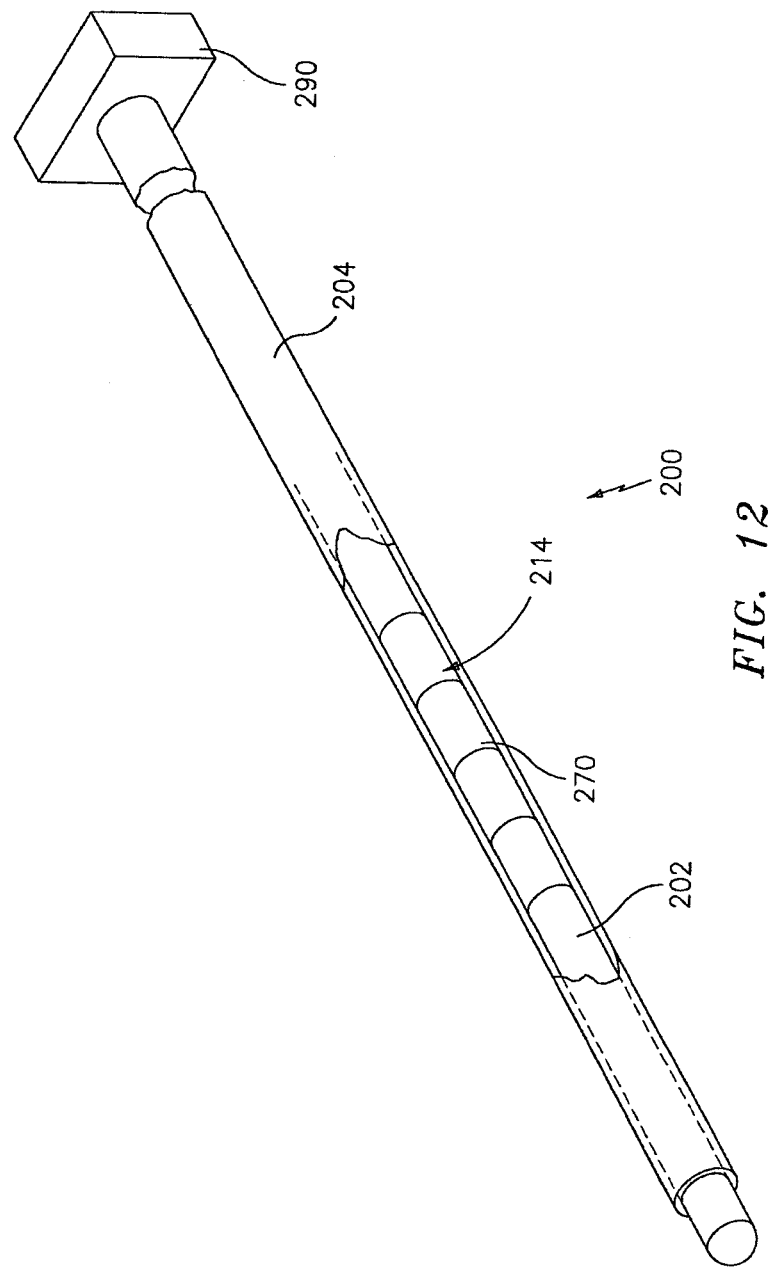
FIG. 12 is a perspective view, partially broken away, of an anastomotic device in accordance with another embodiment of the present disclosure, shown in an insertion and/or withdrawal condition.

As seen in FIG. 12, anchor 214, in the initial condition, has a substantially hollow cylindrical like configuration. However, in the embodiment seen in FIG. 13, the shape and configuration of anchor 214, in the expanded condition, is substantially bell-shaped or fluted. The structural shape of expanded anchor 214 can be controlled by many factors, such as, for example, variations in the radial thickness of anchor 214 when in the initial condition. It is further envisioned that anchor 214 can have a monolithic annular structure in the initial condition or be composed of one or more elements. For example, as shown in FIG. 13, anchor 214 has independent and structurally isolated annular elements 218 separated, for example, by radially aligned walls 220 which are oriented perpendicularly to longitudinal axis "X".

Preferably, anastomotic device 200 includes a sheath 270 positioned over anchor 214 when in the initial condition. The sheath 270 confines anchor 214 when anchor 214 is in the expanded condition. In certain embodiments, sheath 270 is configured and dimensioned to at least partially form or mold the structural shape of anchor 214 when in the expanded condition.

It is further envisioned that the expansion of anchor 214 is controlled by controlling the sequence of the application of fluid or moisture to anchor 214 and/or controlling the structural shape of anchor 214 utilizing sheath 270.

Sheath 270 is desirably a stretchable layer of mesh-type material configured for positioning over at least a portion of anchor 214. Sheath 270 can include a distal end portion and a proximal end portion which can be removably attached to an outer surface of inner tubular sleeve 202. Alternatively, sheath 270 can be positioned at least partially between a distal and a proximal terminal edge of sponge 214 and can also be made from a bio-absorbable material.

Sheath 270 may have a perforated structure, and/or be comprised of a web, mesh, membrane, or other material. In certain embodiments, sheath 270 is disposed over anchor 214 so that sheath 270 is in a rolled or folded configuration when anchor 214 is in the initial configuration and then sheath 270 unfolds to a second configuration when anchor 214 is expanded. For example, as seen in FIG. 13, sheath 270 can provide a graduated proximal slope configured to at least partially advantageously position and align the tissues to be joined (i.e., bladder "B" and urethra "U"). Sheath 270 can also be configured to be severable or detachable and ultimately removed through outer tubular sleeve 204 after anchor 214 has expanded and is set in the expanded condition.

Figure 14:
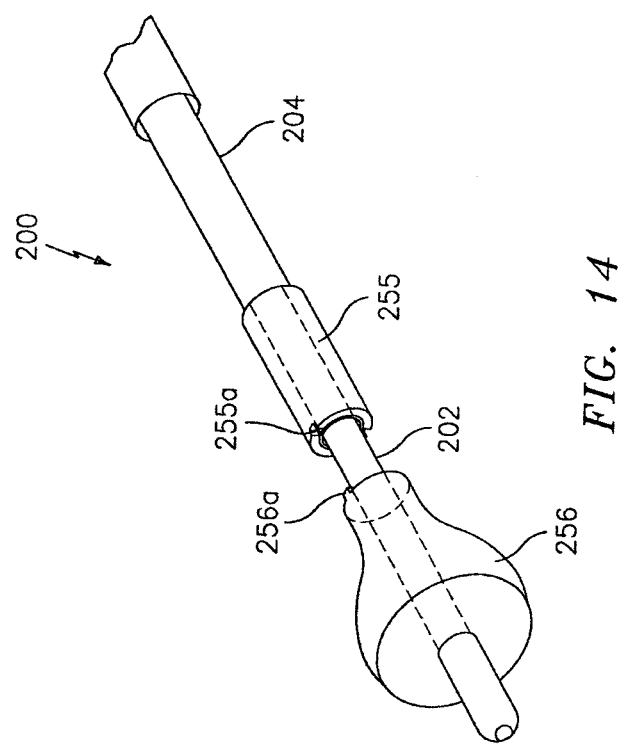
FIG. 14 is an enlarged perspective view of the distal end of an anastomotic device in accordance with the embodiment of FIGS. 12-13, illustrating an alternative arrangement for an anchor.

As seen in FIG. 14, anastomotic device 200 can include a first anchor 255 positioned on outer tubular sleeve 204 and a second anchor 256 positioned on inner tubular sleeve 202. Each anchor 255, 256 is independently movable with respect to one another and independently expandable. The independent movement and expansion of first and second anchor 255, 256 can enable the fixing of anastomotic device 200 to a first vessel (e.g., urethra "U") and the movement of a second vessel (e.g., bladder "B") relative to the first vessel to thereby position the first and second vessels for the anastomosis. Anchors 255 and 256 can be configured to have corresponding or interlocking interfaces 255a, 256a, respectively, or a separate connecting member for maintaining the tissue portions in direct contact with one another.

Figure 15:
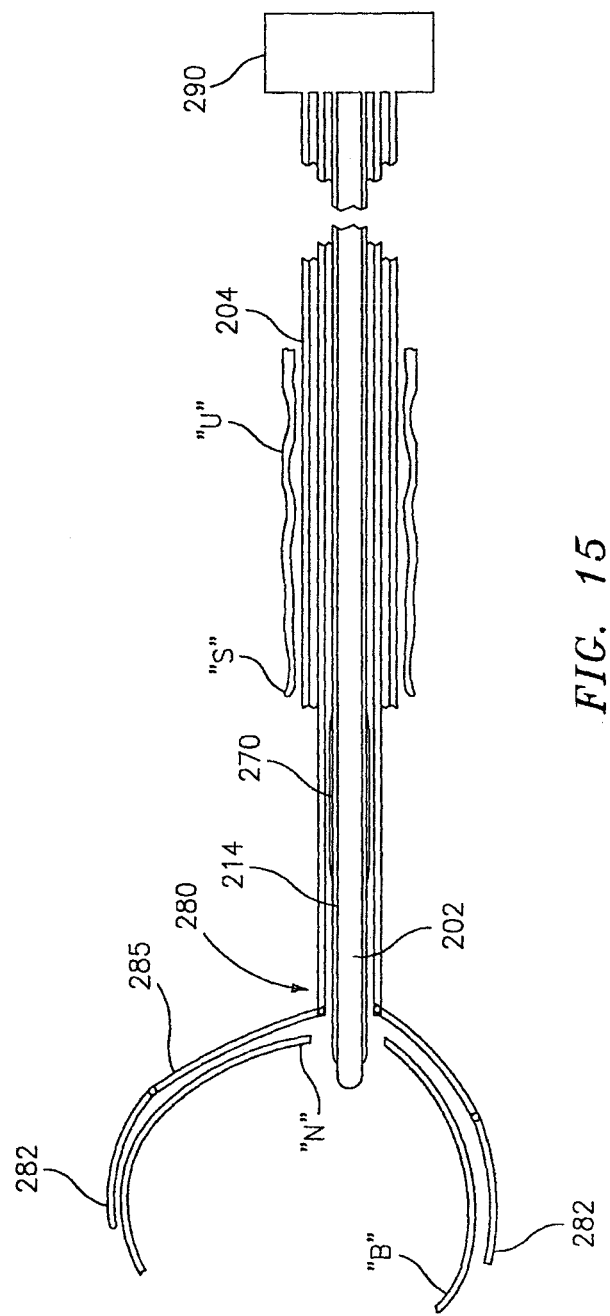
FIG. 15 is a partial cross-sectional view illustrating the passage of an anastomotic device in accordance with the embodiment of FIGS. 12-14 through the urethra and at least partially into the bladder with a grasper repositioning the bladder relative to the urethra.
Figure 16:
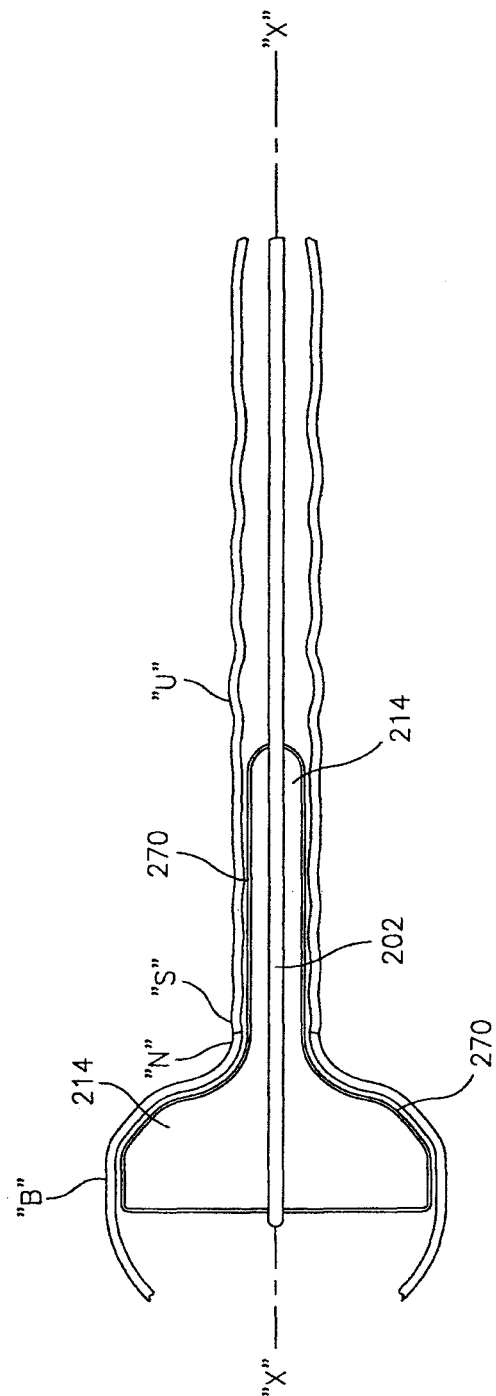
FIG. 16 is a partial cross-sectional view illustrating an anastomotic device in accordance with the embodiment of FIGS. 12-15 in the fully deployed or anchoring condition with the bladder and urethra held in apposition to one another by the expansion of the sponge to the second condition.
Figure 17:
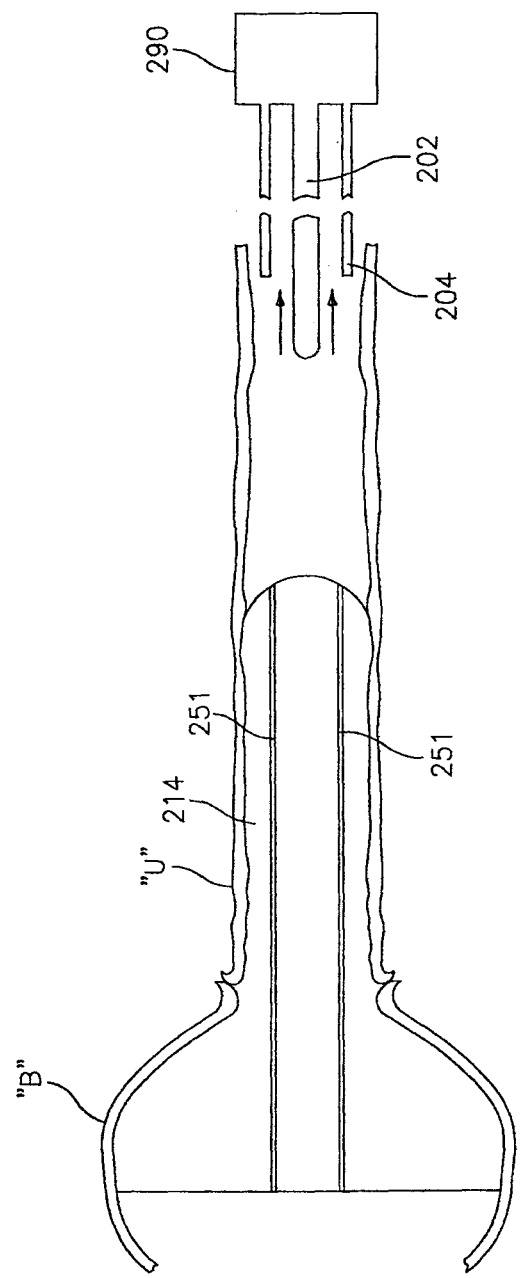
FIG. 17 is a partial cross-sectional view illustrating an anastomotic device in accordance with the embodiment of FIGS. 12-16 being withdrawn from the bladder and urethra while the sponge remains in situ at the anastomotic site bridging the bladder and urethra.

In operation, as seen in FIGS. 15-17, anastomotic device 200 is initially in a first position for trans-urethral passage through urethra "U" and into bladder "B". In the first position anastomotic device 200 includes an anchor 214 in the initial configuration, provided near distal end 208 of inner tubular sleeve 202. The inner tubular sleeve 202 and anchor 214 are slidable within outer tubular sleeve 204.

Anastomotic device 200 is then distally advanced through urethra "U" such that distal end 208 of inner tubular sleeve 202 at least partially enters bladder "B" and, preferably, such that a distal end portion of anchor 214 is disposed within bladder "B". With the distal end portion of anchor 214 positioned at least partially within bladder "B", outer tubular sleeve 204 is withdrawn exposing a portion of the inner tubular sleeve 202 and at least a portion of anchor 214 to bladder "B" and urethra "U".

As seen in FIG. 15, in certain preferred embodiments, inner tubular sleeve 202 is configured for use with a grasper or positioning device 280 which grasper 280 is configured and adapted to aid in the positioning of the vessels. In the embodiment shown, positioning device 280 includes a distal end portion 282, a proximal end 284, and an expandable/retractable jaw portion 285 operatively coupled to distal end portion 282. Control and operation (e.g., expansion and retraction) of expandable jaw portion 285 is performed from control portion 290 and may be achieved through means known in the art such as a mechanical or electro-mechanical connection as well as fluid connections. Positioning device 280 is used to reposition a vessel, preferably, bladder "B", either from the exterior or from the interior of the vessel. In one preferred embodiment, positioning device 280 is slidingly engaged within inner tubular sleeve 202 such that jaws 285 are positionable distally of distal end portion 208 for the movement of the second vessel.

Urethra "U" is moved into position, if required, by using a separate expandable portion positioned on outer tubular sleeve 204 (not shown), or by the expansion of a portion of anchor 214 positioned within urethra "U" and in the vicinity of urethral stump "S" of urethra "U".

In use, positioning device 280 is introduced through outer tubular sleeve 204 or inner tubular sleeve 202 and expanded either within or without bladder "B". Positioning device 280 is then manipulated to reposition bladder "B" relative to inner and outer tubular sleeves 202, 204 such that bladder neck "N" is repositioned substantially along longitudinal axis "X" and, more particularly, such that bladder neck "N" is in apposition and axially aligned with urethral stump "S" of urethra "U" for the subsequent anastomosis. Preferably, the relative movements of outer tubular sleeve 204, inner tubular sleeve 202, positioning device 280, and expansion of anchor 214 or a separate expandable portion are performed remotely from control portion 290.

With the distal end portion of sponge 214 exposed within bladder "B", as seen in FIGS. 16 and 17, sponge 214 is expanded from the initial condition to the expanded condition using control portion 290 to introduce a fluid (e.g., sterile water) from an external source 292 through passageways defined in inner tubular sleeve 202. The fluid is disseminated into anchor 214 in order to expand anchor 214 into a predetermined shape or configuration in the expanded condition.

The annular thickness of anchor 214 while in the compressed condition on inner tubular sleeve 202 determines the thickness of anchor 214 when in the expanded condition. Thus, the configuration of anchor 214 in the expanded condition can be controlled, in one, manner by varying and controlling the amount of sponge material located at a given point along the length of anchor 214 when in the initial condition. Accordingly, those areas of anchor 214 having more anchor material will have a greater amount of radial expansion when moisture or water is applied thereto. Alternatively, anchor 214 may comprise a compressible material, such as a sponge, that is sized to expand upon removal of the outer tubular sleeve. The sleeve may be partially withdrawn so as to allow a first portion of the anchor to expand. After approximating the body vessels, the outer tubular sleeve is further withdrawn to allow the remainder or a second portion of the anchor to expand. The first and second portions of the anchor are sized for engagement with the particular vessels.

Sheath 270 may be positioned over at least a portion of anchor 214 and can include barbs, surgical glue, gripping undulations, or surface treatments (not shown), for example, that can enhance the gripping and positioning of sheath 270 and anchor 214 relative to bladder "B" and urethra "U". Sheath 270 can be configured to enhance the bonding area of the anastomosis directly and/or to facilitate the expansion and shaping of anchor 214 such that anchor 214 is configured for engagement with particular body vessels, such as sustaining a degree of compressive force from bladder neck "N" and urethra "U".

With the distal portion of anchor 214 in the expanded condition, inner and outer tubular sleeves 202, 204 are withdrawn until a proximal end portion of anchor 214 is positioned within urethra "U". Outer tubular sleeve 204 is then further withdrawn to completely expose the proximal end portion of anchor 214. With the proximal end portion of anchor 214 exposed, moisture is applied to the proximal end portion in order to cause the compressed proximal end portion of anchor 214 radially expand. Preferably, the proximal end portion of anchor 214 radially expands such that urethra "U" exerts a radial compressive force to the proximal end of anchor 214.

Outer tubular sleeve 204 can be fully withdrawn from the patient upon the expansion of anchor 214 into the expanded condition. Inner tubular sleeve 202, if configured as a catheter, may remain in position for drainage during the period of the anastomosis or anchor 214 may have a structure sufficiently porous to define at least one passageway 251 oriented generally parallel with longitudinal axis "X". Passageways 251 can be suitable for passing liquids and/or selected solids depending upon the application of anastomotic device 200. When anchor 214 is configured with passageways 251, inner tubular sleeve 202 may be withdrawn together with outer tubular sleeve 204 upon the setting of anchor 214 in the fully expanded condition.

In an alternative preferred method of use, after positioning of anchor 214 within bladder "B" and urethra "U", portions of anchor 214 are expanded in a controlled sequence by the expansion of a proximal portion of anchor 214 in urethra "U" and expansion of a distal portion of anchor 214 in bladder "B". The expansion of the proximal portion fixes urethra 100 in position. The expansion of the distal end portion of anchor 214 is performed sequentially from the distal most end in a proximal direction such that the expansion of the distal end portion of anchor 214 creates a proximally directed driving force intended to reposition bladder "B" proximally. The controlled expansion of anchor 214 is guided and controlled by the diffusion of moisture through selected passageways (not shown) defined in inner tubular sleeve 202 and/or the bounding and guiding of the expansion of anchor 214 by sheath 270, when employed. The directed driving force created by the expansion of the distal end portion of anchor 214 positions bladder "B" and urethra "U" in position for the anastomosis as per the other procedures herein.

The expandable anchor for engaging a body vessel may comprise any expandable structure, including: an onion structure, which comprises a tubular body having a plurality of ribs defining a plurality of longitudinally oriented slots; a balloon or other inflatable structure; a sponge or other device that is expandable upon the introduction of moisture; an anchor having a plurality of flexible arms biased toward an expanded position. The expandable anchor may also comprise the expandable anchors disclosed in certain embodiments of the following PCT Applications, all filed on an even date herewith: Application Entitled Method And Apparatus For Anastomosis Including An Anchoring Sleeve, invented by Scott Manzo; Method And Apparatus For Anastomosis Including An Anchor For Engaging A Body Vessel And Deployable Sutures, invented by Scott Manzo; Method And Apparatus For Anastomosis Including Annular Joining Member, invented by Scott Manzo; Method And Apparatus For Anastomosis Including Annular Joining Member, invented by Scott Manzo; Method And Apparatus For Anastomosis Including An Expandable Anchor, invented by Russell Heinrich and Scott Manzo; Method And Apparatus For Anastomosis Including An Anchoring Sleeve, invented by Scott Manzo; the disclosures of which are all hereby incorporated by reference herein, in their entirety.

The joining member for joining body vessels may comprise any joining member, including: medical adhesive; a sleeve; surgical staples, clips and other fixators; sutures; a balloon or other inflatable structure; a sponge or other device that is expandable upon the introduction of moisture; an anchor having a plurality of flexible arms biased toward an expanded position; an expandable annular body having body vessel engaging features such as protuberances or barbs. The joining member may also comprise the joining members disclosed in certain embodiments of the following PCT Applications, all filed on an even date herewith: Application Entitled Method And Apparatus For Anastomosis Including An Anchoring Sleeve, invented by Scott Manzo; Method And Apparatus For Anastomosis Including An Anchor For Engaging A Body Vessel And Deployable Sutures, invented by Scott Manzo; Method And Apparatus For Anastomosis Including An Anchor For Engaging A Body Vessel And Deployable Sutures, invented by Scott Manzo; Method And Apparatus For Anastomosis Including An Anchoring Sleeve, invented by Scott Manzo; Method And Apparatus For Anastomosis Including Annular Joining Member, invented by Scott Manzo; Method And Apparatus For Anastomosis Including Annular Joining Member, invented by Scott Manzo; Method And Apparatus For Anastomosis Including An Expandable Anchor, invented by Russell Heinrich and Scott Manzo; Method And Apparatus For Anastomosis Including An Anchoring Sleeve, invented by Scott Manzo; the disclosures of which are all hereby incorporated by reference herein, in their entirety.

The methods and apparatus disclosed herein may be used for approximating and/or joining the urethra and bladder, intestinal portions of the body, blood vessels or any other body vessels.

While devices in accordance with the present disclosure have been described as being used in connection with a radical prostatectomy procedure, it is envisioned that devices having a similar structure and mode of operation can be used in various other surgical procedures. It will be understood that various modifications may be made to the embodiments of the presently disclosed device and method disclosed herein.

Therefore, the above description should not be construed as limiting, but merely as an exemplification of a preferred embodiment. Those skilled in the art will envision other modifications within the scope of the present disclosure. For example, the anchor may be shaped for engagement with the particular body vessels upon the introduction of a fluid to the anchor. The anchor may be confined within a sheath or tube so that upon removal of the sheath or tube, the anchor expands, with or without the introduction of a fluid.

What is claimed is:

1. A method of performing a surgical anastomosis, comprising the steps of:

providing a device for performing the surgical anastomosis, the device including:
- a member having a distal end portion and comprising an inner tubular sleeve having a region of porosity formed near the distal end portion;
- a radially expandable anchor operatively disposed at the distal end portion of the member, the expandable anchor being fabricated from at least one of a foam-like and a sponge-like material, and expanded by application of liquid thereto, wherein liquid is introduced through the inner tubular sleeve, through the region of porosity thereof, and to the expandable anchor; and
- a cover disposed over the radially expandable anchor;

passing the device through an opening in a urethra and into a bladder such that a distal end portion of the expandable anchor is positioned at least partially within the bladder;

withdrawing the cover to expose at least the distal end portion of expandable anchor;

expanding at least the distal end portion of the expandable anchor within the bladder such that the expandable anchor engages the bladder;

moving the device until the bladder contacts a distal end of the urethra and a proximal end portion of the expandable anchor is positioned at least partially within the distal end of the urethra;

withdrawing the cover to expose the proximal end portion of the expandable anchor; and expanding the proximal end portion of the expandable anchor within the distal end of the urethra such that the expandable anchor engages the distal end of the urethra.

2. The method according to claim 1, wherein the expandable anchor has a frusto-conical shape when in an expanded condition.

3. The method according to claim 1, wherein the expandable anchor has a thin-walled cylindrical shape when in a compressed condition.

\* \* \* \* \*